(12) United States Patent
Bulliard et al.

(10) Patent No.: US 9,911,920 B2
(45) Date of Patent: Mar. 6, 2018

(54) COMPOUND, ORGANIC PHOTOELECTRONIC DEVICE AND IMAGE SENSOR

(71) Applicant: Samsung Electronics Co., Ltd., Suwon-si, Gyeonggi-do (KR)

(72) Inventors: Xavier Bulliard, Seongnam-si (KR); Tadao Yagi, Hwaseong-si (KR); Rie Sakurai, Suwon-si (KR); Kwang Hee Lee, Yongin-si (KR); Dong-Seok Leem, Hwaseong-si (KR); Hyesung Choi, Seoul (KR); Seon-Jeong Lim, Yongin-si (KR); Yong Wan Jin, Seoul (KR)

(73) Assignee: SAMSUNG ELECTRONICS CO., LTD, Gyeonggi-Do (KR)

( * ) Notice: Subject to any disclaimer, the term of this patent is extended or adjusted under 35 U.S.C. 154(b) by 167 days.

(21) Appl. No.: 14/597,050

(22) Filed: Jan. 14, 2015

(65) Prior Publication Data

US 2016/0020401 A1  Jan. 21, 2016

(30) Foreign Application Priority Data

Jul. 21, 2014 (KR) .................. 10-2014-0092002

(51) Int. Cl.
| | | |
|---|---|---|
| *H01L 51/00* | (2006.01) | |
| *H01L 27/30* | (2006.01) | |
| *C07D 495/14* | (2006.01) | |
| *H01L 51/42* | (2006.01) | |

(52) U.S. Cl.
CPC ........ *H01L 51/0058* (2013.01); *C07D 495/14* (2013.01); *H01L 27/307* (2013.01); *H01L 51/0052* (2013.01); *H01L 51/0067* (2013.01); *H01L 51/0069* (2013.01); *H01L 51/0074* (2013.01); *H01L 51/424* (2013.01)

(58) Field of Classification Search
None
See application file for complete search history.

(56) References Cited

U.S. PATENT DOCUMENTS

| | | | |
|---|---|---|---|
| 8,378,338 | B2 | 2/2013 | Aso et al. |
| 8,686,408 | B2 | 4/2014 | Yofu et al. |
| 2014/0005411 | A1 | 1/2014 | Wong et al. |
| 2014/0008619 | A1 | 1/2014 | Lee et al. |

FOREIGN PATENT DOCUMENTS

| | | | |
|---|---|---|---|
| JP | 2012031373 A | | 2/2012 |
| JP | 2013145677 A | | 7/2013 |
| KR | 20100099225 A | | 9/2010 |
| KR | 20130009953 A | | 1/2013 |
| KR | 2014-0006597 A | | 1/2014 |
| WO | WO2014026244 | * | 2/2014 |

OTHER PUBLICATIONS

Marco et al., Efficient second-order non-linear optical chromophores based on dithienothiophene and thienothiophene bridges. Tetrahedron, 2013, 69, 3919-3926.*

* cited by examiner

*Primary Examiner* — Alicia L Otton
*Assistant Examiner* — Po-Chih Chen
(74) *Attorney, Agent, or Firm* — Harness, Dickey & Pierce, P.L.C.

(57) ABSTRACT

A compound is represented by Chemical Formula 1:

$$X^1\text{-}T\text{-}X^2$$

wherein T is a substituted or unsubstituted fused thiophene moiety, and each of $X^1$ and $X^2$ are independently an organic group including an alkenylene group and an electron withdrawing group.

15 Claims, 11 Drawing Sheets

COMPOUND, ORGANIC PHOTOELECTRONIC DEVICE AND IMAGE SENSOR

CROSS REFERENCE TO RELATED APPLICATIONS

This application claims priority to and the benefit of Korean Patent Application No. 10-2014-0092002 filed in the Korean Intellectual Property Office on Jul. 21, 2014, the entire contents of which are incorporated herein by reference.

BACKGROUND

1. Field

Example embodiments relate to a compound, an organic photoelectronic device and an image sensor.

2. Description of the Related Art

A photoelectronic device converts light into an electrical signal using photoelectronic effects, and may include a photodiode and/or a phototransistor. The photoelectronic device may be applied to an image sensor and/or a solar cell.

An image sensor including a photodiode requires relatively high resolution and thus a relatively small pixel. At present, a silicon photodiode is widely used, but the silicon photodiode has a problem of deteriorated sensitivity and has a relatively small absorption area due to relatively small pixels. Accordingly, an organic material that is capable of replacing silicon has been researched.

The organic material has a relatively high extinction coefficient and selectively absorbs light in a particular wavelength region depending on a molecular structure, and thus may simultaneously replace a photodiode and a color filter and resultantly improve sensitivity and contribute to relatively high integration.

SUMMARY

Example embodiments provide a compound being capable of simultaneously improving light absorption characteristics and wavelength selectivity.

Example embodiments also provide an organic photoelectronic device including the compound.

Example embodiments also provide an image sensor including the organic photoelectronic device.

According to example embodiments, a compound is represented by the following Chemical Formula 1.

$$X^1\text{-}T\text{-}X^2 \quad \text{[Chemical Formula 1]}$$

In the above Chemical Formula 1,

T is a substituted or unsubstituted fused thiophene moiety, and each of $X^1$ and $X^2$ are independently an organic group including an alkenylene group and an electron withdrawing group.

The alkenylene group links the substituted or unsubstituted fused thiophene moiety with the electron withdrawing group, and the electron withdrawing group is one of a substituted or unsubstituted heterocyclic group including at least one of nitrogen, oxygen, and sulfur, a substituted or unsubstituted cycloalkyl group having at least one of a carbonyl group and a thiocarbonyl group, a substituted or unsubstituted heterocyclic group having at least one of a carbonyl group and a thiocarbonyl group, a substituted or unsubstituted aryl group, a combination thereof, and a fused form of the combination thereof.

The electron withdrawing group may be an organic group represented by one of the following Chemical Formulae 2a to 2d.

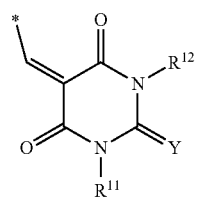

[Chemical Formula 2a]

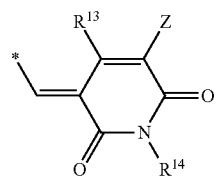

[Chemical Formula 2b]

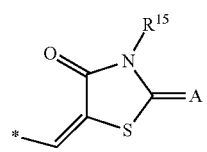

[Chemical Formula 2c]

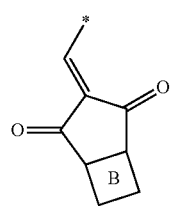

[Chemical Formula 2d]

In the above Chemical Formulae 2a to 2d, each of $R^{11}$ to $R^{15}$ is independently one of hydrogen, a substituted or unsubstituted organic group, and a combination thereof, Y is one of a sulfur atom (S) and an oxygen atom (O), Z is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a cyano group, and a combination thereof, A is a heterocyclic group including at least one of a sulfur atom (S), an oxygen atom (O), a cyano group (CN)-containing group, a nitrogen atom (N), and a sulfur atom (S), and a combination thereof, and B is a substituted or unsubstituted $C_6$ to $C_{30}$ aryl group.

The electron withdrawing group may be selected from the following Group 1.

[Group 1]

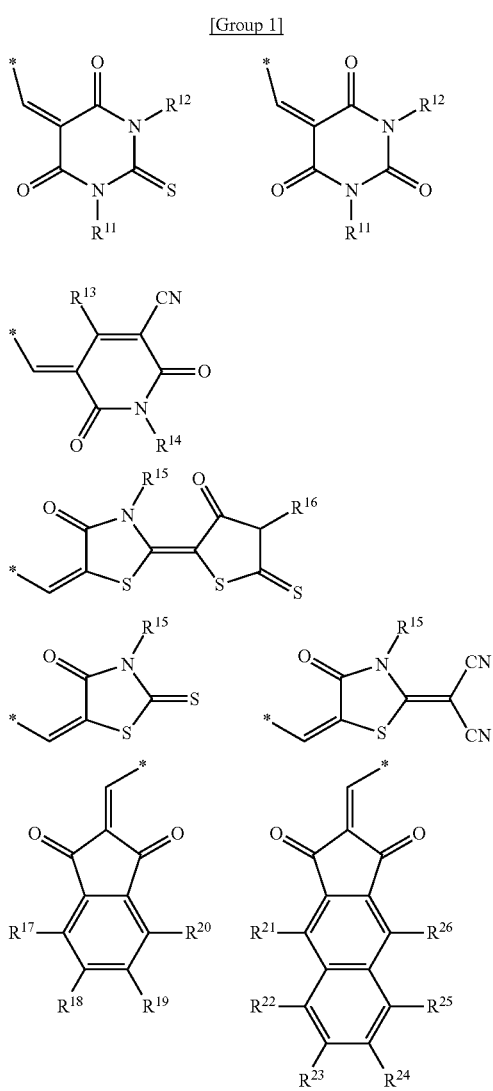

Herein, each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

The fused thiophene moiety may include 3 to 7 thiophene rings.

The compound may be represented by one of the following Chemical Formulae 1a to 1c.

[Chemical Formula 1a]

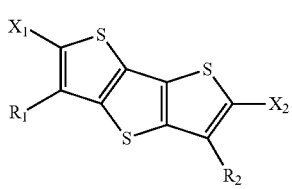

[Chemical Formula 1b]

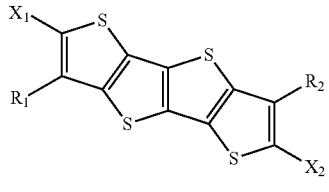

[Chemical Formula 1c]

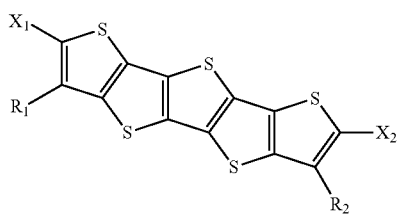

In the above Chemical Formulae 1a to 1c, each of $X^1$ and $X^2$ are independently an organic group including an alkenylene group and an electron withdrawing group, and each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

The compound may selectively absorb light in a green wavelength region.

The green wavelength region may have a maximum absorption wavelength ($\lambda_{max}$) of about 470 nm to about 580 nm.

According to example embodiments, an organic photoelectronic device includes an anode and a cathode facing each other and an active layer between the anode and the cathode, the active layer including the compound.

The organic photoelectronic device may selectively absorb light in a green wavelength region.

The active layer may further include one of N,N'-dimethylquinacridone (DMQA), N,N'-dimethyl-2,9-dimethylquinacridone (DMMQA), a compound represented by the following Chemical Formula 3, and a combination thereof.

[Chemical Formula 3]

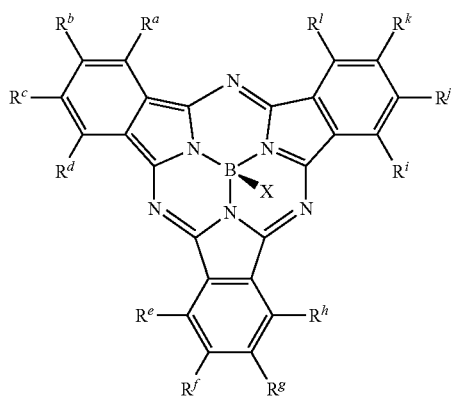

In the above Chemical Formula 3, each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof, and X is an anion.

According to example embodiments, an image sensor includes the organic photoelectronic device.

The image sensor may further include a semiconductor substrate integrated with a plurality of first photo-sensing device sensing light in a blue wavelength region and a plurality of second photo-sensing device sensing light in a red wavelength region, a color filter layer on the semiconductor substrate and including a blue filter selectively absorbing light in a blue wavelength region and a red filter selectively absorbing light in a red wavelength region, and the organic photoelectronic device on the color filter layer.

DETAILED DESCRIPTION

Figure 1:
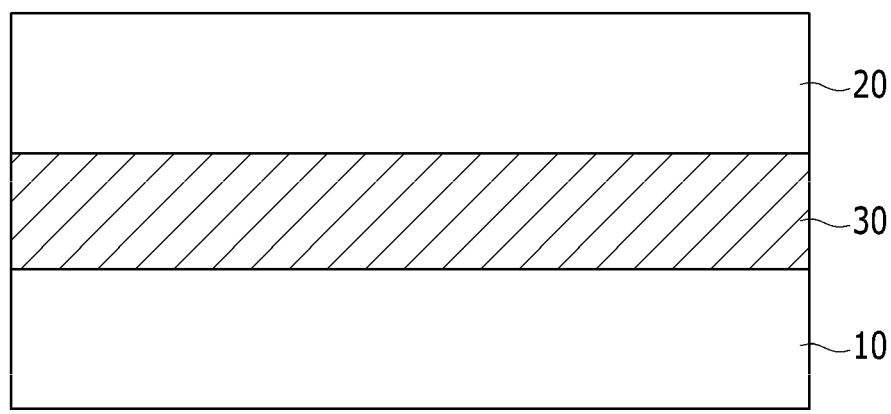
FIG. 1 is a cross-sectional view showing an organic photoelectronic device according to example embodiments.

Example embodiments will hereinafter be described in detail, and may be more easily performed by those who have common knowledge in the related art. However, this disclosure may be embodied in many different forms and is not construed as limited to the example embodiments set forth herein.

It will be understood that when an element or layer is referred to as being "on," "connected to," "coupled to," or "covering" another element or layer, it may be directly on, connected to, coupled to, or covering the other element or layer, or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/ or" includes any and all combinations of one or more of the associated listed items.

It will be understood that, although the terms first, second, third, etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the example embodiments.

Spatially relative terms, e.g., "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of the example embodiments. As used herein, the singular forms "a," "an," and "the" are intended to include the plural forms as well, unless the context clearly indicates otherwise. It will be further understood that the terms "comprises," "comprising," "includes," and/or "including," if used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art. It will be further understood that terms, including those defined in commonly used dictionaries, should be interpreted as having a meaning that is consistent with their meaning in the context of the relevant art and will not be interpreted in an idealized or overly formal sense unless expressly so defined herein.

As used herein, when a definition is not otherwise provided, the term "substituted" refers to one substituted with a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a $C_1$ to $C_{20}$ alkyl group, a $C_2$ to $C_{20}$ alkenyl group, a $C_2$ to $C_{20}$ alkynyl group, a $C_6$ to $C_{30}$ aryl group, a $C_7$ to $C_{30}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{30}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen of a compound.

As used herein, when specific definition is not otherwise provided, the term "hetero" refers to one including 1 to 3 heteroatoms selected from N, O, S, and P.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, a compound according to example embodiments is described.

A compound according to example embodiments is represented by the following Chemical Formula 1.

$$X^1\text{-}T\text{-}X^2 \qquad \text{[Chemical Formula 1]}$$

In the above Chemical Formula 1,

T is a substituted or unsubstituted fused thiophene moiety, and each of $X^1$ and $X^2$ are independently an organic group including an alkenylene group and an electron withdrawing group.

The compound has a structure including a substituted or unsubstituted fused thiophene moiety (T) as a core and organic groups ($X^1$ and $X^2$) positioned at both sides of the core.

The fused thiophene moiety refers to a moiety formed by fusing a plurality of thiophene rings, and the number of the thiophene rings may be, for example, about 3 to about 7, about 3 to about 6, or about 3 to about 5, but is not limited thereto.

The compound includes each organic group at both sides of the fused thiophene moiety, and these two organic groups ($X^1$ and $X^2$) may be, for example, the same, but is not limited thereto. Hereinafter, the organic group is described.

The organic groups ($X^1$ and $X^2$) have an alkenylene group and an electron withdrawing group, and their positions in the organic groups are not particularly limited. For example, the alkenylene group may be positioned between the fused thiophene moiety and the electron withdrawing group, and link them with each other.

The organic groups ($X^1$ and $X^2$) have an electron withdrawing group to provide electron withdrawing properties to the compound. For example, the electron withdrawing group may be a substituted or unsubstituted heterocyclic group including at least one of nitrogen, oxygen, and sulfur; a substituted or unsubstituted cycloalkyl group having at least one of a carbonyl group and a thiocarbonyl group; a substituted or unsubstituted heterocyclic group having at least one of a carbonyl group and a thiocarbonyl group; a substituted or unsubstituted aryl group; combination thereof; or a fused form of the combination thereof, but is not limited thereto.

For example, the electron withdrawing group may be an organic group represented by the following Chemical Formulae 2a to 2d, but is not limited thereto.

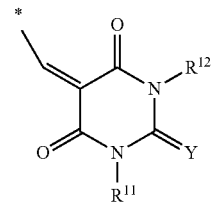

[Chemical Formula 2a]

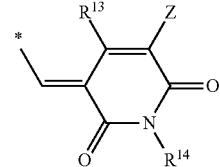

[Chemical Formula 2b]

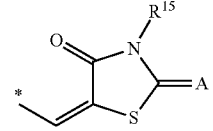

[Chemical Formula 2c]

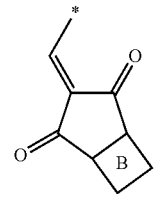

[Chemical Formula 2d]

In the above Chemical Formulae 2a to 2d, each of $R^{11}$ to $R^{15}$ is independently one of hydrogen, a substituted or unsubstituted organic group, and a combination thereof, Y is one of a sulfur atom (S) and an oxygen atom (O), Z is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a cyano group, and a combination thereof, A is a heterocyclic group including at least one of a sulfur atom (S), an oxygen atom (O), a cyano group (CN)-containing group, a nitrogen atom (N), and a sulfur atom (S), and a combination thereof, and B is a substituted or unsubstituted $C_6$ to $C_{30}$ aryl group.

More specifically, the electron withdrawing group may be, for example one selected from the following Group 1.

[Group 1]

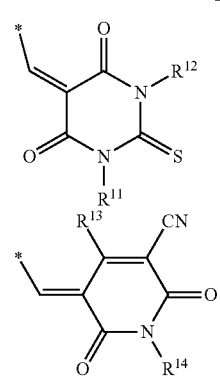

-continued

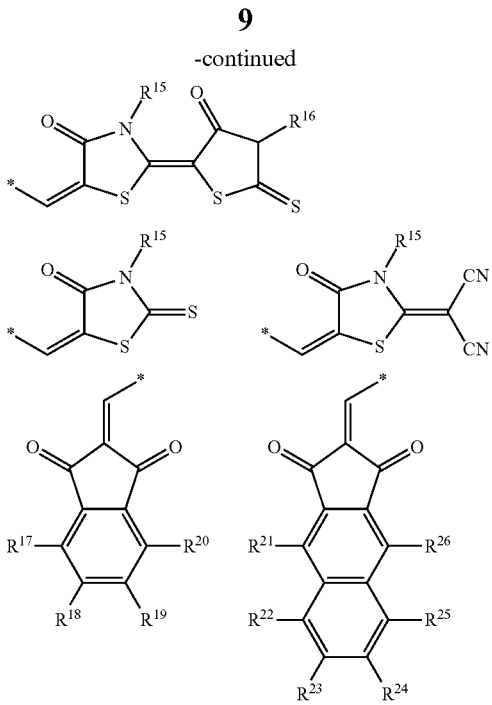

Herein, each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

As described above, the compound has a structure where the fused thiophene moiety (T) is substituted with two cyclic groups having electron withdrawing properties, and may be, for example, represented by the following Chemical Formulae 1a to 1c, but is not limited thereto.

[Chemical Formula 1a]

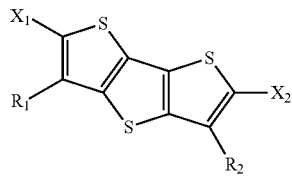

[Chemical Formula 1b]

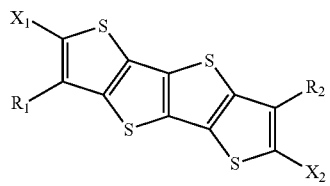

[Chemical Formula 1c]

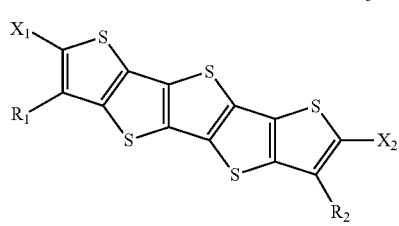

In the above Chemical Formulae 1a to 1c, each of $X^1$ and $X^2$ are independently an organic group including an alkenylene group and an electron withdrawing group, and each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_M$ heteroaryl group, a substituted or unsubstituted $C_1$ to $C_{30}$ alkoxy group, a substituted or unsubstituted $C_2$ to $C_{30}$ alkenyl group, and a combination thereof.

The compound represented by one of the above Chemical Formulae 1a to 1c includes each organic group ($X^1$ and $X^2$) at both sides of the fused thiophene moiety of the core. The organic groups ($X^1$ and $X^2$) may be linked with the outermost right and the outermost left thiophene rings of the fused thiophene moiety, and may be, for example, linked with the carbon that is adjacent to the sulfur atom in the outermost right and the outermost left thiophene rings.

Properties of the compound represented by one of the above Chemical Formulae 1a to 1c may be controlled by substituents ($X^1$, $X^2$, $R^1$, and $R^2$). For example, $X^1$ and $X^2$ may control light absorption characteristics of the compound, and $R^1$ and $R^2$ may control solubility of the compound.

The compound may selectively absorb light in a green wavelength region, for example about 470 nm to about 580 nm, having a maximum absorption wavelength ($\lambda_{max}$). The compound may have a HOMO level of about 5.5 to about 6.8 eV, and an energy bandgap of about 1.5 to about 2.5 eV. When the compound has the HOMO level and energy bandgap within the range, the compound may be applied as a semiconductor effectively absorbing light in a green wavelength region, and thus has relatively high external quantum efficiency (EQE) to improve photoelectric conversion efficiency.

The compound may show a light absorption curve having a relatively narrow full width at half maximum (FWHM) of about 50 nm to about 170 nm in a thin film state. Herein, the FWHM is a width of a wavelength corresponding to a half of a maximum absorption point, and a smaller width at half maximum indicates selective absorption of light in a relatively narrow wavelength region and relatively high wavelength selectivity. Accordingly, a compound having a FWHM within the range may have high selectivity for a green wavelength region.

Hereinafter, an organic photoelectronic device including the compound according to example embodiments is described referring to the drawings.

FIG. 1 is a cross-sectional view showing an organic photoelectronic device according to example embodiments.

Referring to FIG. 1, an organic photoelectronic device 100 according to example embodiments includes a first electrode 10 and a second electrode 20 facing each other, and an active layer 30 interposed between the first electrode 10 and the second electrode 20.

One of the first electrode 10 and the second electrode 20 is an anode and the other is a cathode. At least one of the first electrode 10 and the second electrode 20 may be a light-transmitting electrode, and the light-transmitting electrode may be made of, for example, a transparent conductor, e.g., indium tin oxide (ITO) or indium zinc oxide (IZO), or a metal thin layer of a thin monolayer or multilayer. When one of the first electrode 10 and the second electrode 20 is a non-light-transmitting electrode, the one of the first electrode 10 and the second electrode 20 may be made of, for example, an opaque conductor (e.g., aluminum (Al)).

The active layer 30 includes a p-type semiconductor material and an n-type semiconductor material to form a pn junction, and absorbs external light to generate excitons and then separates the generated excitons into holes and electrons.

The active layer 30 includes the above compound.

The above compound may, for example, selectively absorb light in a green wavelength region, and the active layer 30 may selectively absorb light in a green wavelength having a maximum absorption wavelength ($\lambda_{max}$) at about 470 nm to about 580 nm.

The active layer 30 may show a relatively narrow light absorption curve having a full width at half maximum (FWHM) of about 50 nm to about 170 nm. Accordingly, the active layer 30 may have high selectivity for light in a green wavelength region.

The compound may be an n-type semiconductor or a p-type semiconductor in the active layer 30. When the compound is applied as an n-type semiconductor, a p-type semiconductor may be further included with the n-type semiconductor to form a pn junction, and while when the compound is applied as a p-type semiconductor, an n-type semiconductor may be further included with the p-type semiconductor to form a pn junction.

For example, when the compound is an n-type semiconductor, for example one or more kinds of a p-type semiconductor selected from N,N'-dimethylquinacridone (DMQA), N,N'-dimethyl-2,9-dimethylquinacridone (DMMQA), and a compound represented by the following Chemical Formula 3 may be further included.

[Chemical Formula 3]

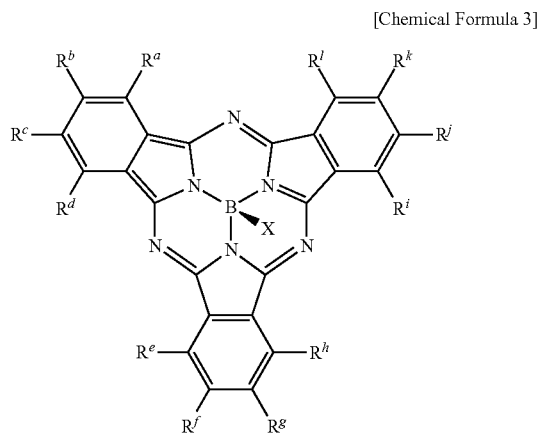

In the above Chemical Formula 3, each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof, and X is an anion.

For example, the X may be a halogen or $OSiR^{13}R^{14}R^{15}$ in the compound represented by the following Chemical Formula 3a, but is not limited thereto.

[Chemical Formula 3a]

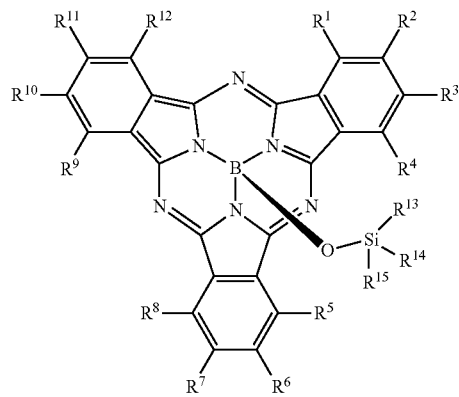

In the above Chemical Formula 3a, each of $R^1$ to $R^{12}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof, and each of $R^{13}$ to $R^{15}$ are independently one of a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a substituted or unsubstituted amine group, a substituted or unsubstituted $C_6$ to $C_{30}$ arylamine group, a substituted or unsubstituted silyl group, and a combination thereof.

The active layer 30 may be a single layer or a multilayer. The active layer 30 may be, for example, an intrinsic layer (1 layer), a p-type layer/1 layer, an 1 layer/n-type layer, a p-type layer/1 layer/n-type layer, and/or a p-type layer/n-type layer.

The intrinsic layer (1 layer) may include the p-type semiconductor compound and the n-type semiconductor compound in a ratio of about 1:100 to about 100:1. The compounds may be included in a ratio ranging from about 1:50 to about 50:1 within the range, specifically, about 1:10 to about 10:1, and more specifically, about 1:about 1. When the p-type and n-type semiconductors have a composition ratio within the range, an exciton may be effectively produced and a pn junction may be effectively formed.

The p-type layer may include the p-type semiconductor, and the n-type layer may include the n-type semiconductor.

The active layer 30 may have a thickness of about 1 nm to about 500 nm, and specifically, about 5 nm to about 300 nm. When the active layer 30 has a thickness within the range, the active layer may effectively absorb light, effectively separate holes from electrons, and deliver them, thereby effectively improving photoelectric conversion efficiency.

In the organic photoelectronic device 100, when light enters from the first electrode 10 and/or second electrode 20, and when the active layer 30 absorbs light having a predetermined or given wavelength region, excitons may be produced from the inside. The excitons are separated into holes and electrons in the active layer 30, and the separated holes are transported to an anode that is one of the first electrode 10 and second electrode 20 and the separated electrons are transported to the cathode that is the other of and the first electrode 10 and second electrode 20 so as to flow a current in the organic photoelectronic device.

Figure 2:
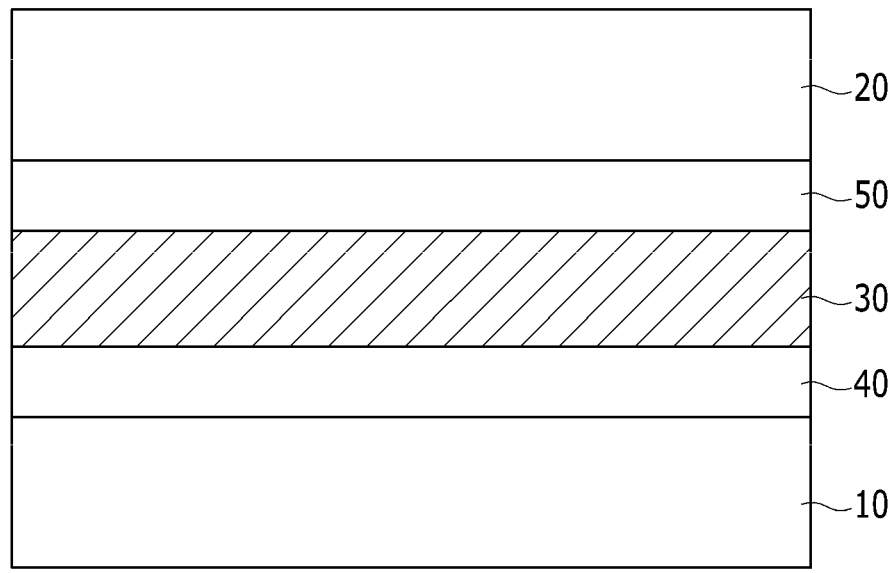
FIG. 2 is a cross-sectional view showing an organic photoelectronic device according to example embodiments.

Referring to FIG. 2, an organic photoelectronic device according to example embodiments is described.

FIG. 2 is a cross-sectional view of an organic photoelectronic device according to example embodiments.

Referring to FIG. 2, an organic photoelectronic device 200 according to example embodiments includes a first electrode 10 and a second electrode 20 facing each other, and an active layer 30 interposed between the first electrode 10 and the second electrode 20, like the example embodiment illustrated in FIG. 1.

However, the organic photoelectronic device 200 according to example embodiments may further include charge auxiliary layers 40 and 50 between the first electrode 10 and the active layer 30, and the second electrode 20 and the active layer 30, unlike the example embodiment illustrated in FIG. 1. The charge auxiliary layers 40 and 50 may facilitate the transfer of holes and electrons separated from the active layer 30, so as to increase efficiency.

The charge auxiliary layers 40 and 50 may be at least one selected from a hole injection layer (HIL) for facilitating hole injection, a hole transport layer (HTL) for facilitating hole transport, an electron blocking layer (EBL) for preventing or inhibiting electron transport, an electron injection layer (EIL) for facilitating electron injection, an electron transport layer (ETL) for facilitating electron transport, and a hole blocking layer (HBL) for preventing or inhibiting hole transport.

The charge auxiliary layers 40 and 50 may include, for example, an organic material, an inorganic material, or an organic/inorganic material. The organic material may be an organic compound having hole or electron characteristics, and the inorganic material may be, for example, a metal oxide (e.g., molybdenum oxide, tungsten oxide, and nickel oxide).

The hole transport layer (HTL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron blocking layer (EBL) may include one selected from, for example, poly(3,4-ethylenedioxythiophene):poly(styrenesulfonate) (PEDOT:PSS), polyarylamine, poly(N-vinylcarbazole), polyaniline, polypyrrole, N,N,N',N'-tetrakis(4-methoxyphenyl)-benzidine (TPD), 4-bis[N-(1-naphthyl)-N-phenyl-amino]biphenyl (α-NPD), m-MTDATA, 4,4',4"-tris(N-carbazolyl)-triphenylamine (TCTA), and a combination thereof, but is not limited thereto.

The electron transport layer (ETL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

The hole blocking layer (HBL) may include one selected from, for example, 1,4,5,8-naphthalene-tetracarboxylic dianhydride (NTCDA), bathocuproine (BCP), LiF, $Alq_3$, $Gaq_3$, $Inq_3$, $Znq_2$, $Zn(BTZ)_2$, $BeBq_2$, and a combination thereof, but is not limited thereto.

Either one of the charge auxiliary layers 40 and 50 may be omitted.

The organic photoelectronic device may be applied to various fields, for example a solar cell, an image sensor, a photo-detector, a photo-sensor, and an organic light emitting diode (OLED), but is not limited thereto.

Hereinafter, an example of an image sensor including the organic photoelectronic device is described referring to drawings. As an example of an image sensor, an organic CMOS image sensor is described.

Figure 3:
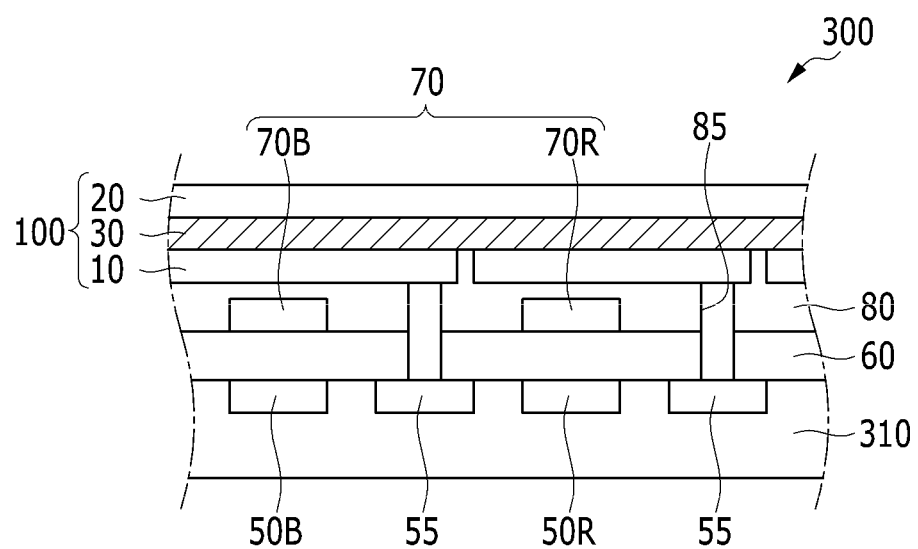
FIG. 3 is a cross-sectional view showing an organic CMOS image sensor according to example embodiments.

FIG. 3 is a cross-sectional view showing an organic CMOS image sensor according to example embodiments.

FIG. 3 illustrates blue, green, and red pixels that are adjacent to one another, but is not limited thereto.

Referring to FIG. 3, an organic CMOS image sensor 300 according to example embodiments includes a semiconductor substrate 310 integrated with photo-sensing devices 50B and 50R, a transmission transistor (not shown), and a charge storage device 55, a lower insulation layer 60, a color filter 70, an upper insulation layer 80, and an organic photoelectronic device 100.

The semiconductor substrate 310 may be a silicon substrate, and is integrated with the photo-sensing device 50, a transmission transistor (not shown), and a charge storage device 55. The photo-sensing devices 50B and 50R may be photodiodes.

The photo-sensing devices 50B and 50R, the transmission transistor, and/or the charge storage device 55 may be integrated in each pixel, and as shown in the drawing, the photo-sensing devices 50B and 50R may be included in a blue pixel and a red pixel and the charge storage device 55 may be included in a green pixel.

The photo-sensing devices 50B and 50R sense light, the information sensed by the photo-sensing devices may be transferred by the transmission transistor, and the charge storage device 55 is electrically connected with the organic photoelectronic device 100, so the information of the charge storage device 55 may be transferred by the transmission transistor.

A metal wire (not shown) and a pad (not shown) are formed on the semiconductor substrate 310. In order to decrease signal delay, the metal wire and pad may be made of a metal having relatively low resistivity, for example, aluminum (Al), copper (Cu), silver (Ag), and alloys thereof, but is not limited thereto. However, the structure is also not limited, and the metal wire and pad may be positioned under the photo-sensing devices 50B and 50R.

The lower insulation layer 60 is formed on the metal wire and the pad. The lower insulation layer 60 may be made of an inorganic insulating material, e.g., a silicon oxide and/or a silicon nitride, or a low dielectric constant (low K) material, e.g., SiC, SiCOH, SiCO, and SiOF. The lower insulation layer 60 has a trench exposing the charge storage device 55. The trench may be filled with fillers.

A color filter 70 is formed on the lower insulation layer 60. The color filter 70 includes a blue filter 70B formed in the blue pixel and a red filter 70R filled in the red pixel. In example embodiments, a green filter is not included, but a green filter may be further included.

The upper insulation layer 80 is formed on the color filter 70. The upper insulation layer 80 eliminates a step caused by the color filters 70 and smoothes the surface. The upper insulation layer 80 and lower insulation layer 60 may include a contact hole (not shown) exposing a pad, and a through-hole 85 exposing the charge storage device 55 of a green pixel.

The organic photoelectronic device 100 is formed on the upper insulation layer 80. The organic photoelectronic device 100 includes the first electrode 10, the active layer 30, and the second electrode 20 as described above.

The first electrode 10 and the second electrode 20 may be transparent electrodes, and the active layer 30 selectively absorbs light in a green wavelength, region as described above and replaces a color filter of a green pixel.

When light enters from the second electrode 20, the light in a green wavelength region may be mainly absorbed in the active layer 30 and photoelectrically converted, while the light in the rest of the wavelength regions passes through the first electrode 10 and may be sensed in photo-sensing devices 50B and 50R.

Figure 4:
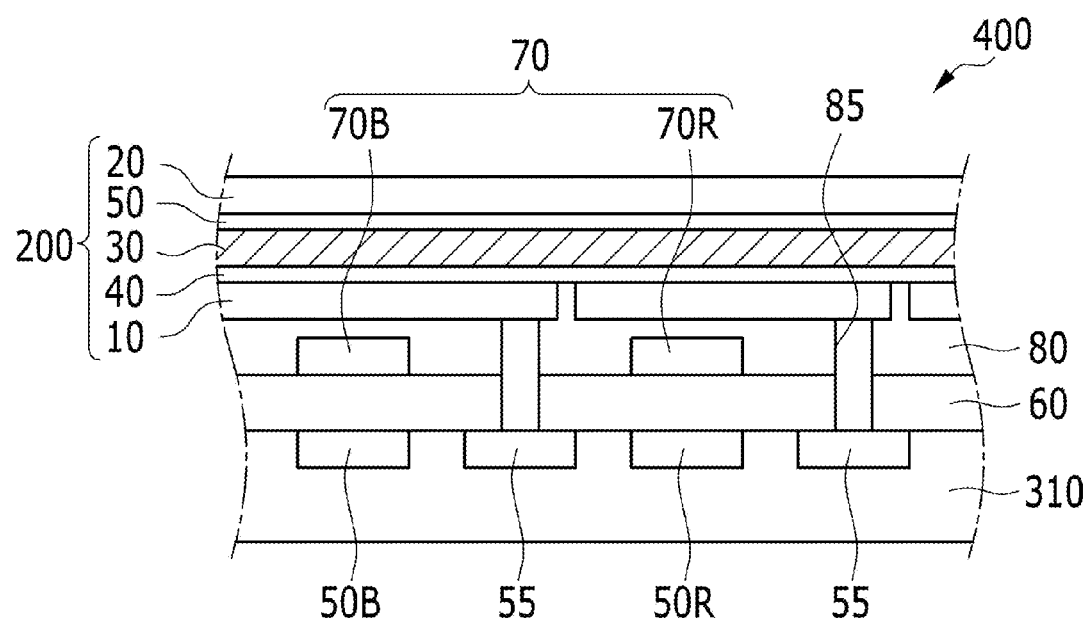
FIG. 4 is a cross-sectional view showing an organic CMOS image sensor according to example embodiments.
Figure 5:
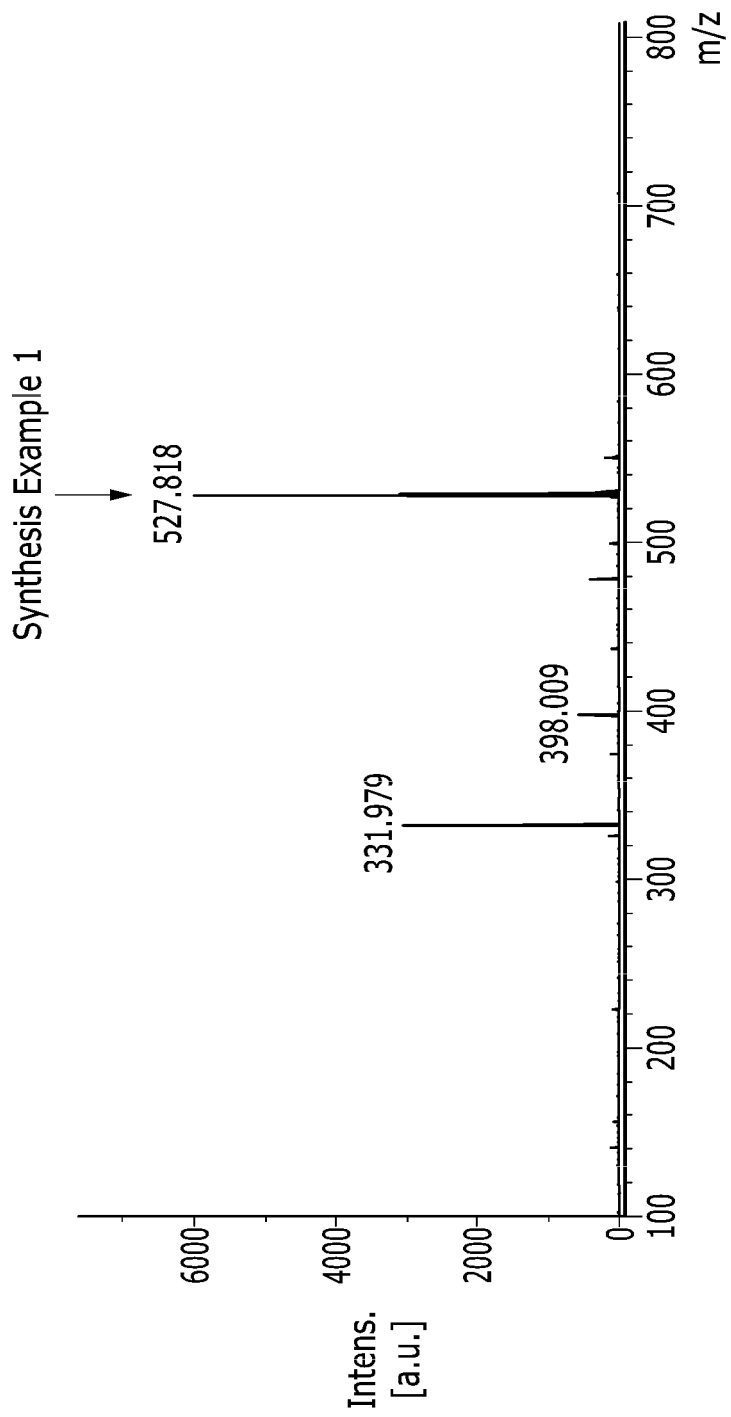
FIG. 5 shows MALDI-TOF mass analysis data of the compound according to Synthesis Example 1.
Figure 6:
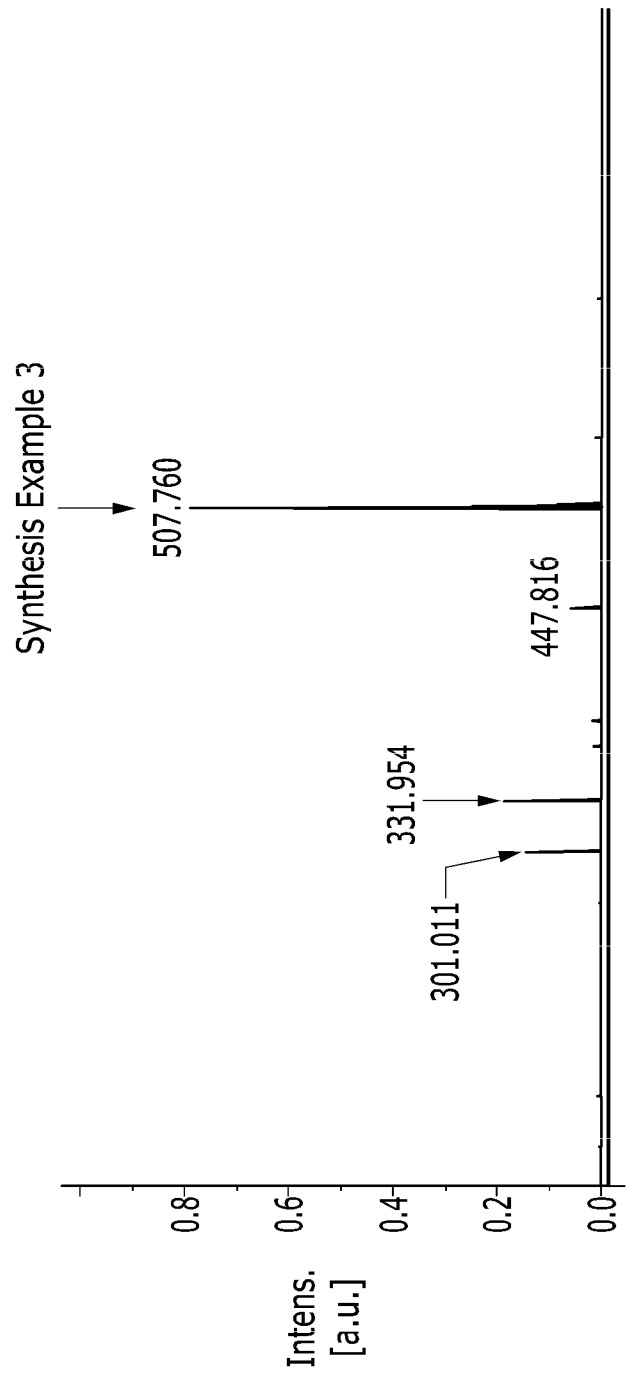
FIG. 6 shows MALDI-TOF mass analysis data of the compound according to Synthesis Example 3.
Figure 7:
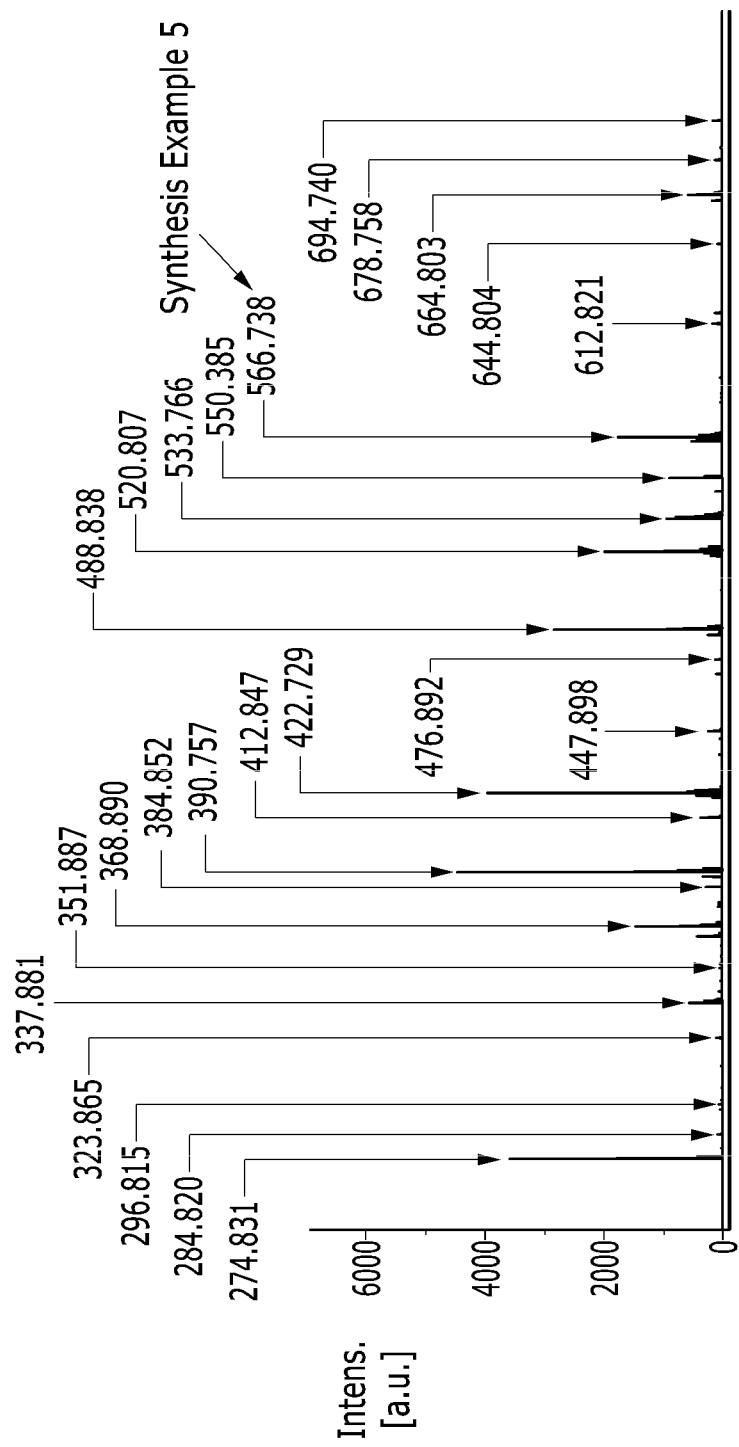
FIG. 7 shows MALDI-TOF mass analysis data of the compound according to Synthesis Example 5.
Figure 8:
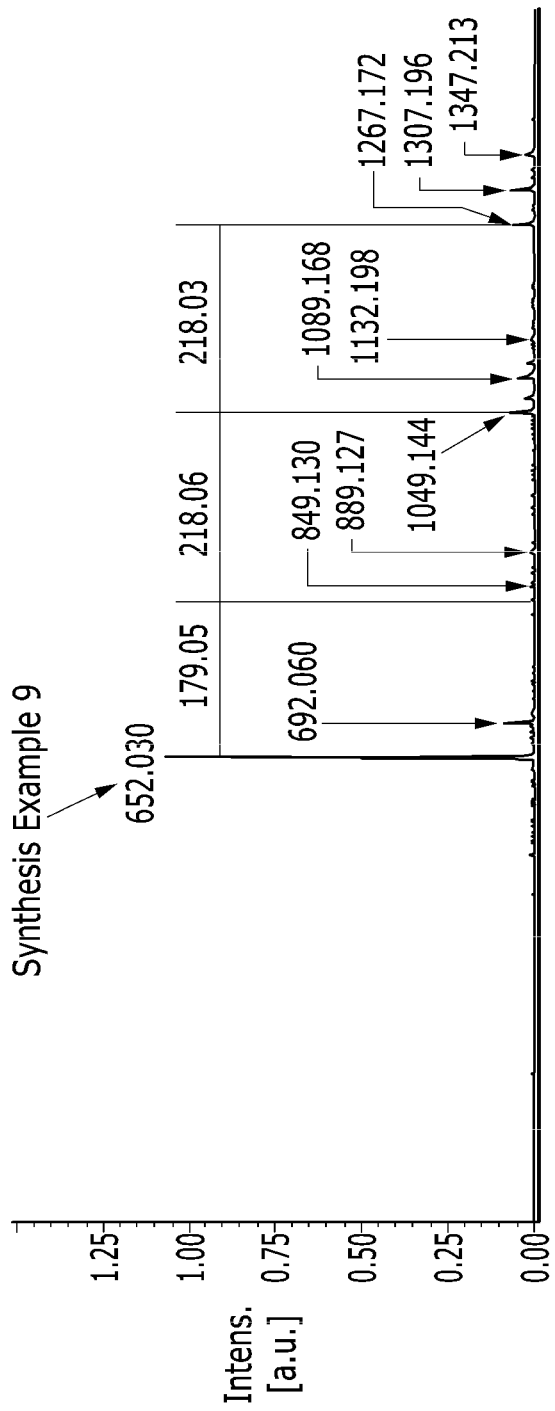
FIG. 8 shows MALDI-TOF mass analysis data of the compound according to Synthesis Example 9.

FIG. 4 is cross-sectional view showing an organic CMOS image sensor according to example embodiments.

Referring to FIG. 4, an organic CMOS image sensor 400 according to example embodiments includes a semiconductor substrate 310 integrated with photo-sensing devices 50B and 50R, a transmission transistor (not shown), a charge storage device 55, a lower insulation layer 60, a color filter 70, an upper insulation layer 80, and an organic photoelectronic device 100, like the example embodiment illustrated in FIG. 3.

However, the organic photoelectronic device 100 further includes charge auxiliary layers 40 and 50. The charge auxiliary layers 40 and 50 are the same as described above, and one of the charge auxiliary layers 40 and 50 may be omitted.

Hereinafter, the present disclosure is illustrated in more detail with reference to examples. However, these are examples, and the present disclosure is not limited thereto.

Synthesis of Compound

Synthesis Example 1

[Reaction Scheme 1]

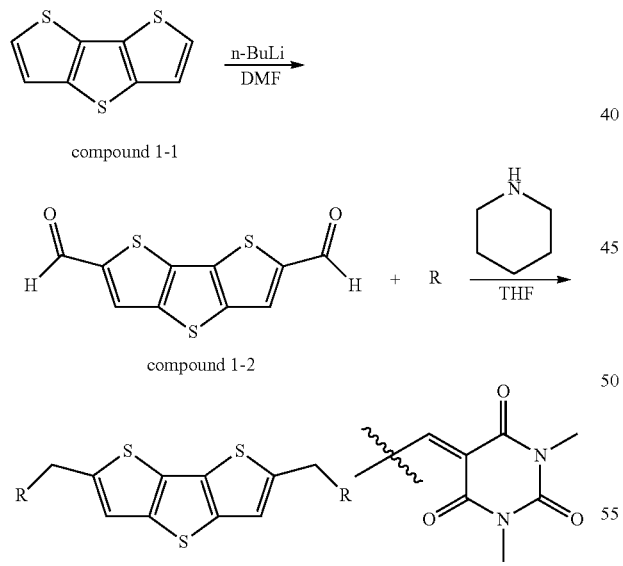

compound 1-1 compound 1-2

A compound is synthesized according to the Reaction Scheme 1.

19.6 g (100 mmol) of dithieno[3,2-b:2',3'-d]thiophene (Sigma-Aldrich Co., Ltd.) (a compound 1-1) is dissolved in 500 ml of anhydrous tetrahydrofuran (THF) under a dry nitrogen stream, and the solution is cooled down to 0° C. Then, 156 ml (250 mmol) of 1.6 M n-butyl lithium is slowly added thereto while the temperature is maintained. The reaction solution is cooled down to −78° C. and agitated for one hour, and then, 22.1 g (300 mmol) of anhydrous dimethyl formamide (DMF) is dripped therein. The mixture is agitated for one hour, and the reaction solution is agitated for 2 hours until the temperature increases to room temperature. Then, the reaction solution is put in 2 L of water, and a solid remaining at the upper part after filtration during the filtration of the precipitated solid is collected and dried, obtaining 20.2 g of dithieno[3,2-b:2',3'-d]thiophene-2,6-dicarbaldehyde (a compound 1-2) (yield: 80%).

Subsequently, 3.78 g (15.0 mmol) of the compound 1-2 and 7.02 g (45 mmol) of dimethyl barbituric acid (Sigma-Aldrich Co., Ltd.) are suspended in 200 ml of THF, piperidine (Sigma-Aldrich Co., Ltd.) in a catalytic amount is added thereto, and the mixture is reacted at 50° C. for 5 hours. A solid remaining at the upper part during filtration of the precipitated dark red solid is obtained and suspended in 250 ml of dimethyl acetamide (DMAc), the suspended solution is agitated at 90° C. for 1 hour, and the unsolved part is refiltered, obtaining a solid remaining at the upper part. This process is repeated once more, obtaining 7.30 g of a compound represented by the following Chemical Formula 1aa (yield: 92%).

[Chemical Formula 1aa]

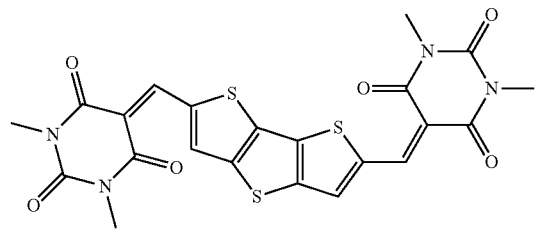

Synthesis Example 2

1,3-dimethyl-2-thiobarbituric acid is synthesized in a method described in J. Pharmacol., 1944, 82, 292. p. 4417. Subsequently, 1.43 g (8.31 mmol) of the obtained 1,3-dimethyl-2-thiobarbituric acid and 0.7 g (2.77 mmol) of the compound are suspended in 37 ml of 1-2 THF, piperidine (Sigma-Aldrich Co., Ltd.) as a catalyst is added thereto, and the mixture is reacted at 50° C. for 5 hours. The solid remaining at the upper part is obtained during filtration of the precipitated black solid and suspended in 53.5 ml of DMAc (dimethyl acetamide), the suspended solution is agitated at 90° C. for 1 hour, and a solid remaining at the upper part is refiltered. This process is repeated once more, obtaining 1.39 g of a compound represented by the following Chemical Formula 1bb (yield: 90%).

[Chemical Formula 1bb]

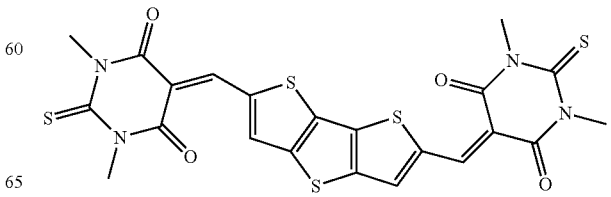

Synthesis Example 3

6.48 g of a compound represented by the following Chemical Formula 1cc (yield: 85%) is obtained according to the same method as Synthesis Example 1, except for using 6.58 g of 1,3-indandione instead of the compound 1-2 according to Synthesis Example 1 and the dimethyl barbituric acid.

[Chemical Formula 1cc]

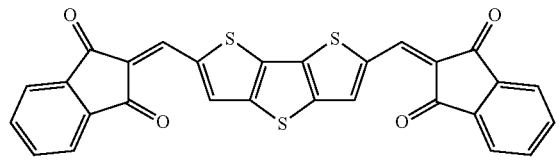

Synthesis Example 4

[Reaction Scheme 2]

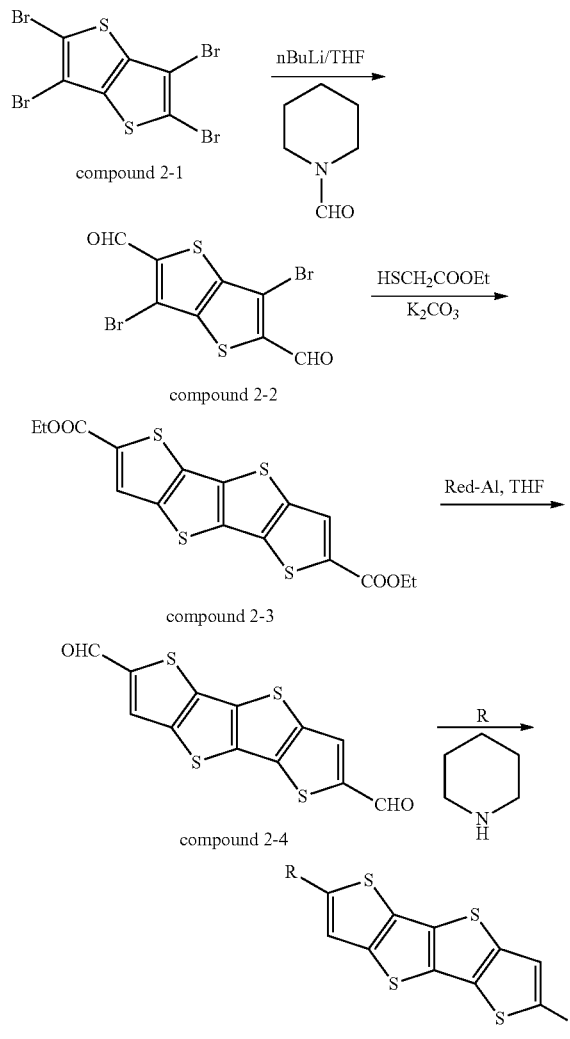

Synthesis is performed according to the Reaction Scheme 2.

Diethyl thieno[v 2',3': 4,5]thieno[3,2-b]thieno[2,3-d]thiophene-2,6-dicarboxylate (a compound 2-3) is synthesized according to a method of Scheme 2 described in Adv. Funct. Mater. 2012, 22, 48-60 p. 50.

4.5 g (11.3 mmol) of the compound 2-3 is suspended in 50 ml of anhydrous THF, and then the suspended solution is cooled down to −20° C. On the other hand, 44.1 ml (136 mmol) of Red-Al (Sigma-Aldrich Co., Ltd.) is mixed with 50 ml of anhydrous THE, and the mixture is cooled down to −10° C. Herein, 16.5 ml of 1-methylpiperazine (Sigma-Aldrich Co., Ltd.) is slowly dripped therein, and the mixture is agitated for 30 minutes to adjust the reducing solution. This reducing solution is slowly dripped in the compound 2-3 mixed solution. The mixture is further agitated for 10 hours by setting its reaction temperature at 50° C. After the reaction, 100 ml of water is slowly added thereto, unreacted Red-Al is quenched, and 1N hydrochloric acid is added thereto until a yellow extract is produced. The precipitated solid is filtered to obtain a solid remaining at the upper part, and the obtained solid is cleaned with MeOH and water. Then, the solid is Soxhlet-extracted with dichloromethane, obtaining 1.05 g of thieno[2',3':4,5]thieno[3,2-b]thieno[2,3-d]thiophene-2,6-dicarbaldehyde (a compound 2-4).

Then, 0.50 g of the compound 2-4 and 0.76 g of dimethyl barbituric acid are used to perform the same reaction as the final step of Synthesis Example 1, obtaining 0.75 g o f a compound represented by the following Chemical Formula 1dd (yield: 80%).

[Chemical Formula 1dd]

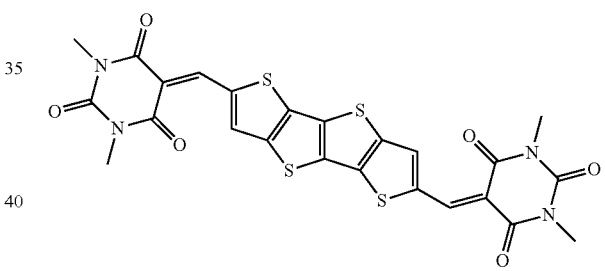

Synthesis Example 5

The same method as Synthesis Example 4 is used for synthesis except for using 1,3-indandione instead of dimethyl barbituric acid. 1.00 g of the compound 2-4 is used with 1.40 g of 1,3-indandione to obtain 1.60 g of a compound represented by the following Chemical Formula 1ee (yield: 90%).

[Chemical Formula 1ee]

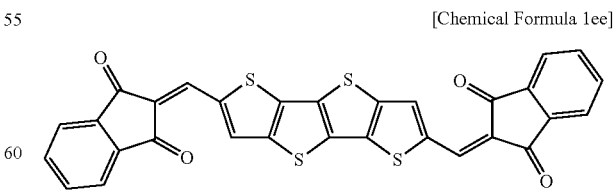

Synthesis Example 6

The same method as Synthesis Example 4 is used for synthesis except for using rhodanine instead of the dimethyl barbituric acid. 1.00 g of the compound 2-4 is used with 1.28 g of rhodanine, obtaining 1.27 g of a compound represented by the following Chemical Formula 1ff (yield: 74%).

[Chemical Formula 1ff]

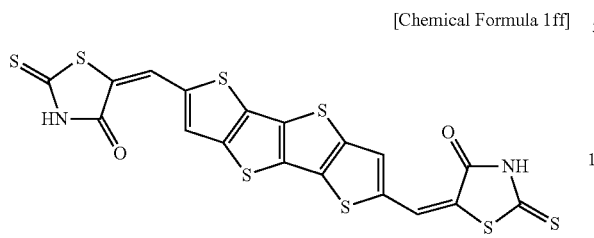

Synthesis Example 7

2-hydrocyclopenta[b]naphthalen-1,3-dione is synthesized in a method described in Chem. Mater., Vol. 18, No. 18, 2006 p. 4261. 1.00 g of the compound 1-2 is used with 2.33 g of 2-hydrocyclopenta[b]naphthalen-1,3-dione according to the same method as Synthesis Example 1, obtaining 1.51 g of a compound represented by the following Chemical Formula 1gg (yield: 65%).

[Chemical Formula 1gg]

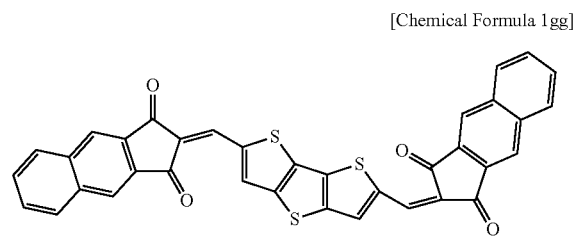 [SMILES: O=C1C(=Cc2cc3sc4cc(C=C5C(=O)c6cc7ccccc7cc6C5=O)sc4c3s2)C(=O)c2cc3ccccc3cc21]

Synthesis Example 8

1.00 g of the compound 2-4 according to Synthesis Example 4 is used with 1.88 g of 2,3-benzo indandione according to the same method as Synthesis Example 4, obtaining 1.28 g of a compound represented by the following Chemical Formula 1hh (yield: 60%).

[Chemical Formula 1hh]

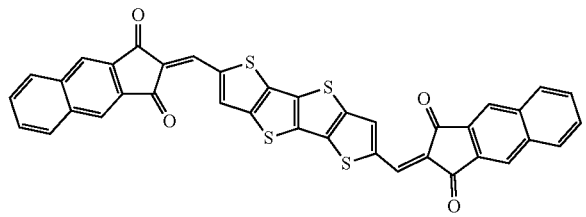

Synthesis Example 9

Tetrafluoro-1,3-indandione is synthesized according to a method described in Eur. J. Org. Chem., Issue 26, 2012. p. 4951.

1.26 g of the compound 1-2 and 3.27 g of tetrafluoro-1,3-indandione are used, obtaining 1.21 g of a compound represented by the following Chemical Formula 1ii according to the same method as Synthesis Example 1 (yield: 40%).

[Chemical Formula 1ii]

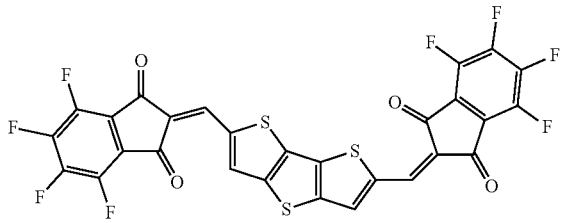

Comparative Synthesis Example 1

A compound represented by the following Chemical Formula A is synthesized (Uhrich, C.; Schueppel, R.; Petrich, A.; Pfeiffer, M.; Leo, K.; Brier, E.; Kilickiran, P.; Baeuerle, P. Organic Thin-Film Photovoltaic Cells Based on Oligothiophenes with Reduced Bandgap. Adv. Funct. Mater. 2007, 17, 2991-2999.).

[Chemical Formula A]

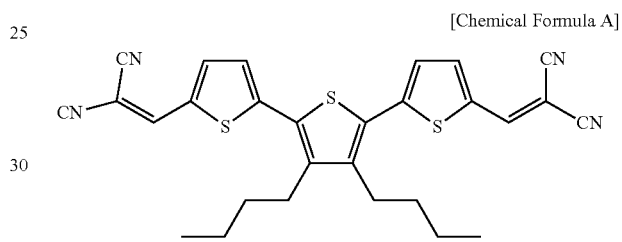

Evaluation I

Evaluation 1

The structure of the compounds according to Synthesis Examples 1 to 8 is examined through MALDI-TOF mass analysis.

FIGS. 5 to 8 show MALDI-TOF mass analysis data of the compounds according to Synthesis Examples 1, 3, 5, and 9.

Referring to FIGS. 5 to 8, the compounds of the synthesis examples are substantially obtained.

Evaluation 2

Light absorption characteristics of the compounds according to Synthesis Examples 1 to 7 and 9 are evaluated.

The light absorption characteristics are evaluated by thermally evaporating each compound according to Synthesis Examples 1 to 7 and 9 to form a 50 to 100 nm-thick thin film under high vacuum (<$10^{-7}$ Torr) at a rate of 0.5 Å/s to 1.0 Å/s, and then radiating an ultraviolet (UV)-visible ray (UV-Vis) thereon with a Cary 5000 UV spectroscope (Varian Inc.).

Maximum absorption wavelength data of each compound are provided in Table 1.

TABLE 1

| | Maximum absorption wavelength ($\lambda_{max}$) (nm) |
|---|---|
| Synthesis Example 1 | 518 |
| Synthesis Example 2 | 512 |
| Synthesis Example 3 | 470 |
| Synthesis Example 4 | 487 |
| Synthesis Example 5 | 516 |

TABLE 1-continued

| | Maximum absorption wavelength ($\lambda_{max}$) (nm) |
|---|---|
| Synthesis Example 6 | 491 |
| Synthesis Example 7 | 491 |
| Synthesis Example 9 | 513 |

Referring to Table 1, the compounds according to Synthesis Examples 1 to 7 and 9 may show a maximum absorption wavelength ($\lambda_{max}$) in a green wavelength region.

In other words, the compounds according to Synthesis Examples 1 to 7 and 9 show improved wavelength selectivity compared with Comparative Synthesis Example 1.

Manufacture of Organic Photoelectronic Device

Example 1

ITO is sputtered on a glass substrate to form an about 100 nm-thick anode, and a molybdenum oxide ($MoO_x$, $0<x\leq3$) is deposited to form a 30 nm-thick thin film as a charge auxiliary layer. Subsequently, a compound (an n-type semiconductor compound) according to Synthesis Example 1 and a compound (a p-type semiconductor compound) represented by the following Chemical Formula 3b in a thickness ratio of 1:1 are co-deposited on the molybdenum oxide thin film to form a 70 nm-thick active layer. Thereafter, Al is sputtered on the active layer to form an 80 nm-thick cathode, manufacturing an organic photoelectronic device.

[Chemical Formula 3b]

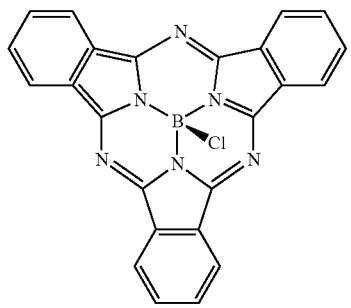

Comparative Example 1

An organic photoelectronic device is manufactured according to the same method as Example 1, except for using the compound according to Comparative Synthesis Example 1 as the n-type semiconductor compound.

Evaluation II

Evaluation 1

External quantum efficiency (EQE) and full width at half maximum (FWHM) of the organic photoelectronic device according to Example 1 are evaluated.

The external quantum efficiency is measured by using an IPCE measurement system (McScience Co., Ltd., Korea). First of all, the IPCE measurement system is calibrated by using a Si photodiode (Hamamatsu Photonics K.K., Japan), then mounted on the organic photoelectronic devices according to Example 1 and Comparative Example 1, and their external quantum efficiency at a wavelength ranging from about 350 to 700 nm is measured at room temperature.

The full width at half maximum (FWHM) is evaluated by measuring the width of a wavelength corresponding to a half of a maximum absorption point in the external quantum efficiency graph.

Figure 9:
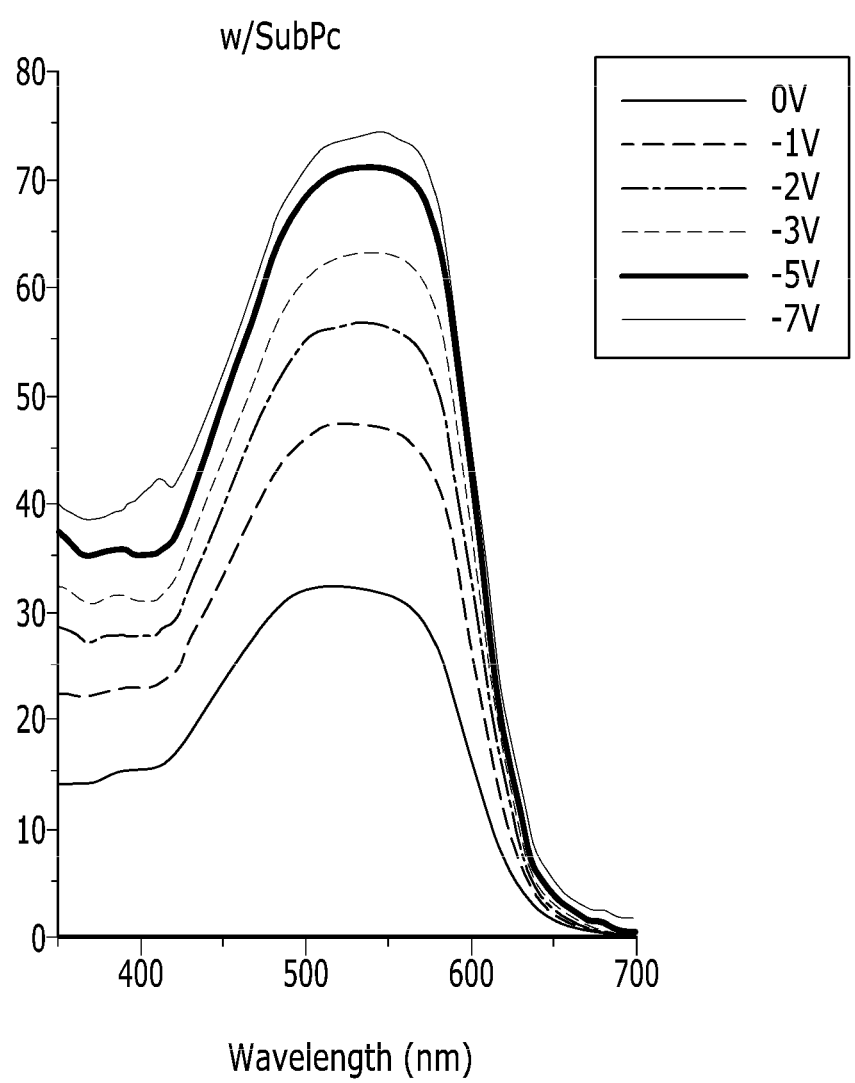
FIG. 9 is a graph showing external quantum efficiency depending on a wavelength of the organic photoelectronic device according to Example 1.
Figure 10:
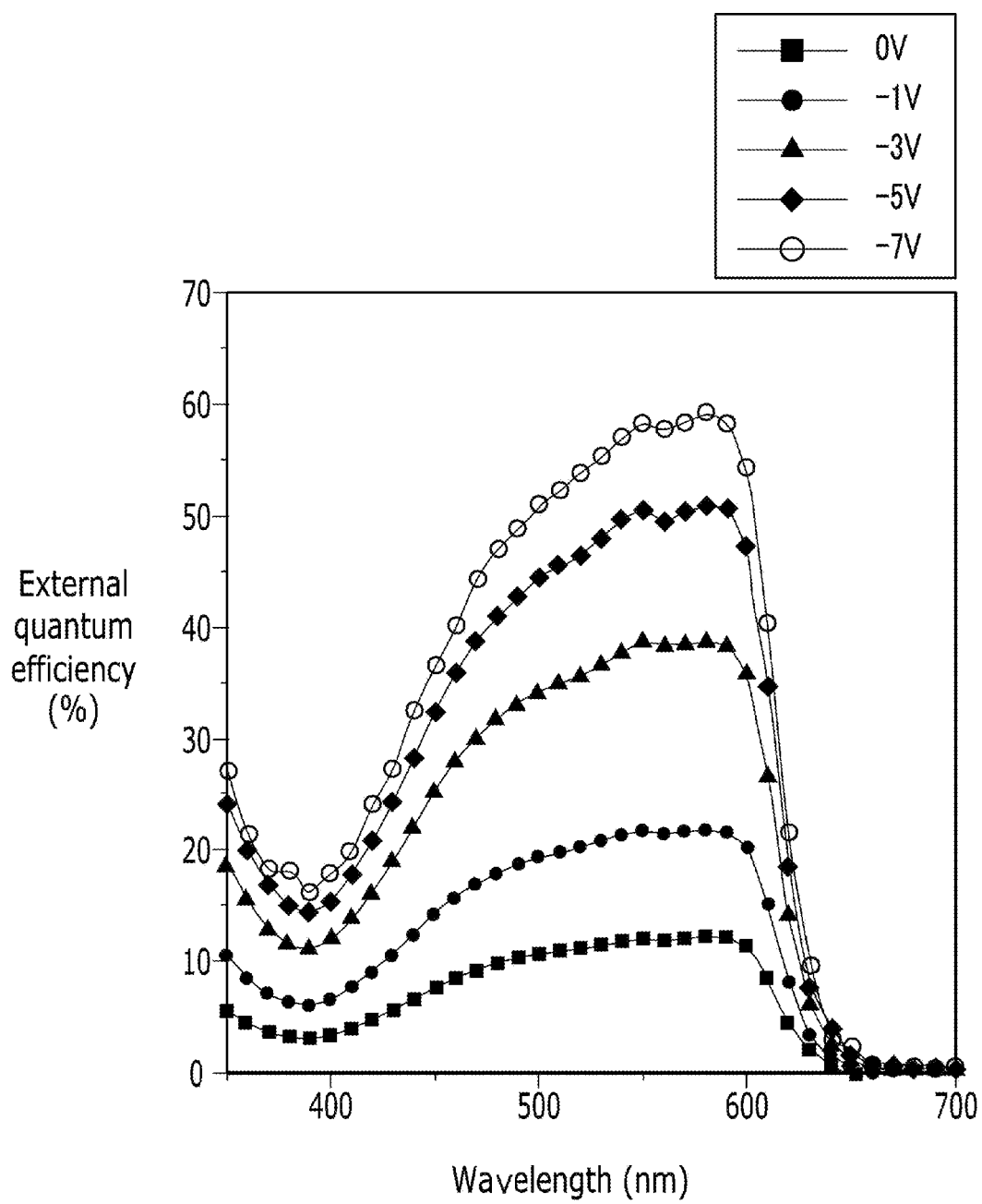
FIG. 10 is a graph showing external quantum efficiency depending on a wavelength of the organic photoelectronic device according to Comparative Example 1.

FIG. 9 is a graph showing external quantum efficiency of the organic photoelectronic device according to Example 1 depending on a wavelength, and FIG. 10 is a graph showing external quantum efficiency of the organic photoelectronic device according to Comparative Example 1 depending on a wavelength.

Referring to FIGS. 9 and 10, the organic photoelectronic device according to Example 1 shows a maximum peak of the external quantum efficiency (EQE) in a green wavelength region, unlike the organic photoelectronic device according to Comparative Example 1.

Table 2 shows the maximum external quantum efficiency ($EQE_{max}$) and the full width at half maximum (FWHM) of the organic photoelectronic devices according to Example 1 and Comparative Example 1 at 0 V and 3 V.

TABLE 2

| | Maximum external quantum efficiency ($EQE_{max}$) (%) | | Full width at half maximum (FWHM) |
|---|---|---|---|
| | 0 V | 3 V | (nm) |
| Example 1 | 32 | 63 | 175 |
| Comparative Example 1 | 12 | 39 | 185 |

Referring to Table 2, the maximum external quantum efficiency ($EQE_{max}$) of the organic photoelectronic device according to Example 1 at 3 V has a relatively high value of greater than 60%.

In addition, the organic photoelectronic device according to Example 1 has a relatively smaller full width at half maximum (FWHM). Accordingly, the organic photoelectronic device has relatively high wavelength selectivity about light in a green wavelength region.

Evaluation 2

External quantum efficiency (EQE) of the organic photoelectronic device according to Example 1 depending on a wavelength is evaluated by changing the room temperature condition into a temperature-increasing condition.

Figure 11:
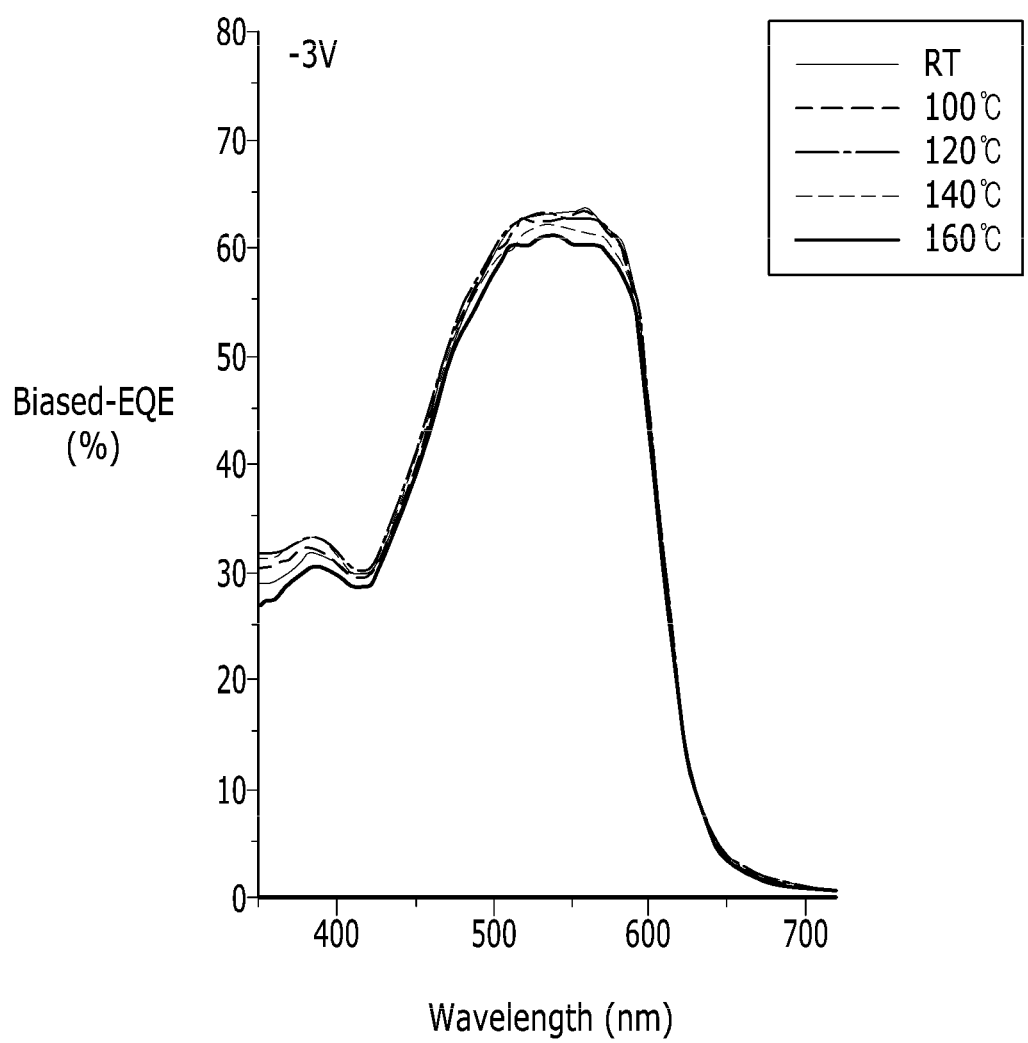
FIG. 11 is a graph showing external quantum efficiency depending on a wavelength of the organic photoelectronic device according to Comparative Example at 3 V.

FIG. 11 is a graph showing external quantum efficiency depending on a wavelength of the organic photoelectronic device according to Comparative Example at 3 V.

Referring to FIG. 11, the organic photoelectronic device according to Example 1 has equivalent external quantum efficiency at 100° C., 120° C., 140° C., and 160° C., and thus shows improved thermal stability.

While this disclosure has been described in connection with what is presently considered to be practical example embodiments, it is to be understood that the inventive concepts are not limited to the disclosed embodiments, but, on the contrary, is intended to cover various modifications and equivalent arrangements included within the spirit and scope of the appended claims.

What is claimed is:

1. A compound represented by the following Chemical Formula 1:

$$X^1\text{-}T\text{-}X^2 \qquad \text{[Chemical Formula 1]}$$

wherein, in the above Chemical Formula 1,

T is a substituted or unsubstituted fused thiophene moiety, and each of $X^1$ and $X^2$ are independently an organic group including an alkenylene group and an electron withdrawing group, wherein the fused thiophene moiety includes 3 to 7 thiophene rings, and wherein the electron withdrawing group is an organic group represented by one of the following Chemical Formulae 2a to 2d:

[Chemical Formula 2a]

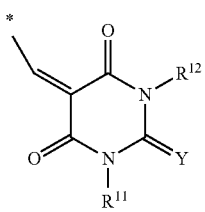

[Chemical Formula 2b]

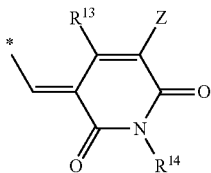

[Chemical Formula 2c]

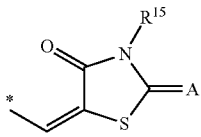

[Chemical Formula 2d]

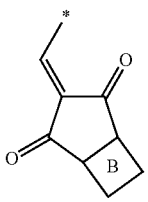

wherein, in the above Chemical Formulae 2a to 2d, each of $R^{11}$ to $R^{15}$ is independently one of hydrogen, a substituted or unsubstituted organic group, or a combination thereof, Y is one of a sulfur atom (S) and an oxygen atom (O), Z is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a cyano group, and a combination thereof, A is a sulfur atom (S), an oxygen atom (O), a cyano group (CN)-containing group, a heterocyclic group including at least one of a nitrogen atom (N) and a sulfur atom (S), or a combination thereof, and B is a substituted or unsubstituted $C_6$ to $C_{30}$ aryl group.

2. The compound of claim 1, wherein the alkenylene group links the substituted or unsubstituted fused thiophene moiety with the electron withdrawing group.

3. The compound of claim 1, wherein the electron withdrawing group is selected from the following Group 1:

[Group 1]

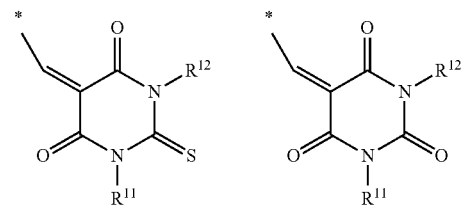

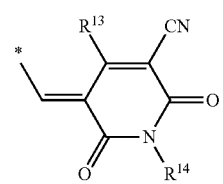

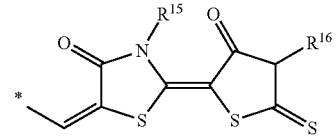

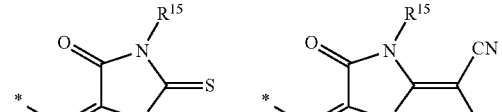

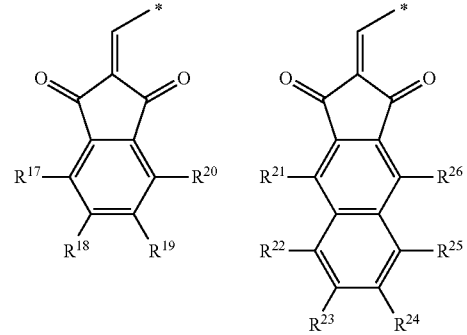

wherein each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

4. The compound of claim 1, wherein the compound is represented by one of the following Chemical Formulae 1a to 1c:

[Chemical Formula 1a]

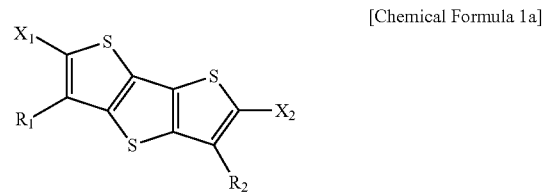

-continued

[Chemical Formula 1b]

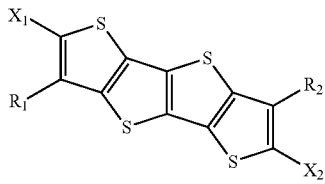

[Chemical Formula 1c]

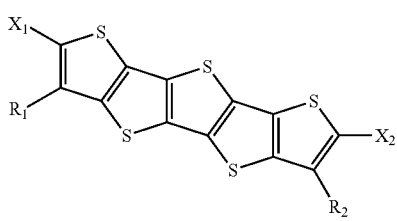

wherein, in the above Chemical Formulae 1a to 1c,
each of $X^1$ and $X^2$ are independently an organic group including an alkenylene group and an electron withdrawing group, and
each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

5. A compound for selectively absorbing light in a green wavelength region and represented by the following Chemical Formula 1:

$X^1$-T-$X^2$  [Chemical Formula 1]

wherein, in the above Chemical Formula 1,
T is a substituted or unsubstituted fused thiophene moiety, and
each of $X^1$ and $X^2$ are independently an organic group including an alkenylene group and an electron withdrawing group,
wherein the fused thiophene moiety includes 3 to 7 thiophene rings, and
wherein the electron withdrawing group is an organic group represented by one of the following Chemical Formulae 2a to 2d:

[Chemical Formula 2a]

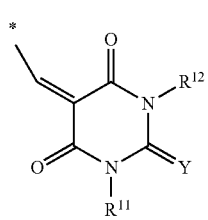

[Chemical Formula 2b]

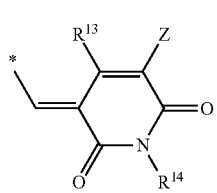

[Chemical Formula 2c]

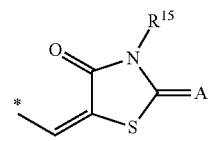

[Chemical Formula 2d]

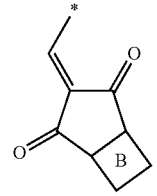

wherein, in the above Chemical Formulae 2a to 2d,
each of $R^{11}$ to $R^{15}$ is independently one of hydrogen, a substituted or unsubstituted organic group, or a combination thereof,
Y is one of a sulfur atom (S) and an oxygen atom (O),
Z is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a cyano group, and a combination thereof,
A is a sulfur atom (S), an oxygen atom (O), a cyano group (CN)-containing group, or a heterocylic group including at least one of a nitrogen atom (N) and a sulfur atom (S), and
B is a substituted or unsubstituted $C_6$ to $C_{30}$ aryl group.

6. The compound of claim 5, wherein the compound has a maximum absorption wavelength ($\lambda_{max}$) of about 470 nm to about 580 nm.

7. An organic photoelectronic device comprising:
an anode and a cathode facing each other; and
an active layer between the anode and the cathode, the active layer including a compound represented by the following Chemical Formula 1:

$X^1$-T-$X^2$  [Chemical Formula 1]

wherein, in the above Chemical Formula 1,
T is a substituted or unsubstituted fused thiophene moiety, and
each of $X^1$ and $X^2$ are independently an organic group including an alkenylene group and an electron withdrawing group,
wherein the fused thiophene moiety includes 3 to 7 thiophene rings, and
wherein the electron withdrawing group is an organic group represented by one of the following Chemical Formulae 2a to 2d:

[Chemical Formula 2a]

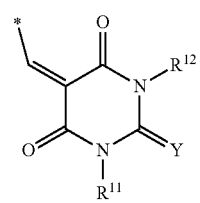

-continued

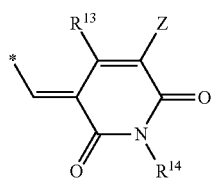
[Chemical Formula 2b]

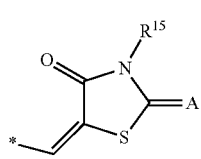
[Chemical Formula 2c]

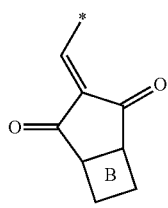
[Chemical Formula 2d]

wherein, in the above Chemical Formulae 2a to 2d, each of $R^{11}$ to $R^{15}$ is independently one of hydrogen, a substituted or unsubstituted organic group, or a combination thereof, Y is one of a sulfur atom (S) and an oxygen atom (O), Z is one of hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_3$ to $C_{30}$ heterocyclic group, a substituted or unsubstituted $C_1$ to $C_{30}$ alkoxy group, a cyano group, and a combination thereof, A is a sulfur atom (S), an oxygen atom (O), a cyano group (CN)-containing group, a heterocyclic group including at least one of a nitrogen atom (N) and a sulfur atom (S), or a combination thereof, and B is a substituted or unsubstituted $C_6$ to $C_{30}$ aryl group.

8. The organic photoelectronic device of claim 7, wherein the alkenylene group links the substituted or unsubstituted fused thiophene moiety with the electron withdrawing group.

9. The organic photoelectronic device of claim 7, wherein the electron withdrawing group is selected from the following Group 1:

[Group 1]

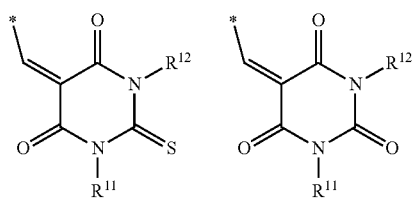

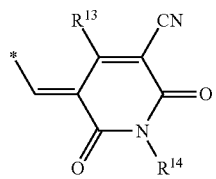
[Chemical Formula 2b]

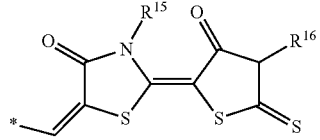
[Chemical Formula 2c]

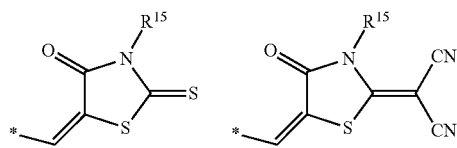

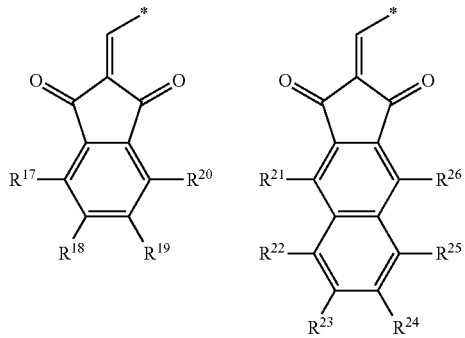

wherein each of $R^{11}$ to $R^{26}$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

10. The organic photoelectronic device of claim 7, wherein the compound is represented by one of the following Chemical Formulae 1a to 1c:

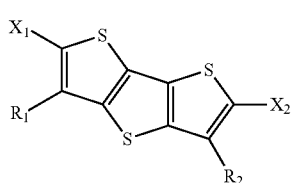
[Chemical Formula 1a]

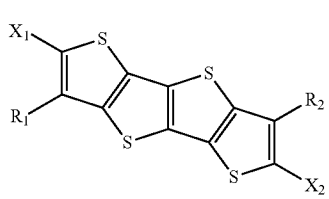
[Chemical Formula 1b]

-continued

[Chemical Formula 1c]

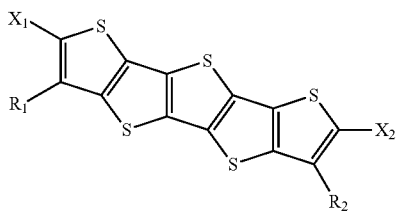

wherein, in the above Chemical Formulae 1a to 1c, each of $X^1$ and $X^2$ are independently an organic group including an alkenylene group and an electron withdrawing group, and each of $R^1$ and $R^2$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, a substituted or unsubstituted $C_1$ to $C_{30}$ alkoxy group, a substituted or unsubstituted $C_2$ to $C_{30}$ alkenyl group, and a combination thereof.

11. The organic photoelectronic device of claim 7, wherein the compound selectively absorbs light in a green wavelength region.

12. The organic photoelectronic device of claim 11, wherein the green wavelength region has a maximum absorption wavelength ($\lambda_{max}$) of about 470 nm to about 580 nm.

13. The organic photoelectronic device of claim 7, wherein the active layer further includes one of N,N'-dimethylquinacridone (DMQA), N,N'-dimethyl-2,9-dimethylquinacridone (DMMQA), a compound represented by the following Chemical Formula 3, and a combination thereof:

[Chemical Formula 3]

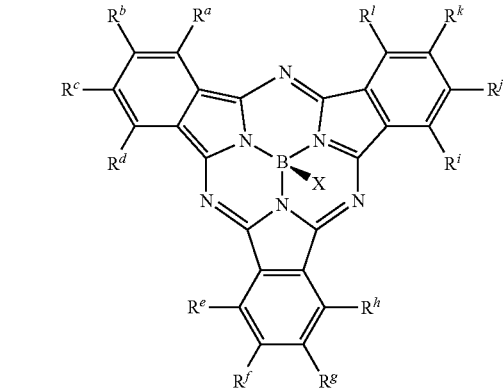

wherein, in the above Chemical Formula 3, each of $R^a$ to $R^l$ are independently one of hydrogen, a substituted or unsubstituted $C_1$ to $C_{30}$ alkyl group, a substituted or unsubstituted $C_6$ to $C_{30}$ aryl group, a substituted or unsubstituted $C_3$ to $C_{30}$ heteroaryl group, and a combination thereof, and X is an anion.

14. An image sensor comprising the organic photoelectronic device of claim 7.

15. The image sensor of claim 14, further comprising:

a semiconductor substrate integrated with a plurality of first photo-sensing device sensing light in a blue wavelength region and a plurality of second photo-sensing device sensing light in a red wavelength region;

a color filter layer on the semiconductor substrate, wherein the color filter layer includes a blue filter selectively absorbing light in a blue wavelength region and a red filter selectively absorbing light in a red wavelength region; and the organic photoelectronic device on the color filter layer.

* * * * *